United States Patent
Saria et al.

(10) Patent No.: US 11,497,417 B2
(45) Date of Patent: Nov. 15, 2022

(54) MEASURING PATIENT MOBILITY IN THE ICU USING A NOVEL NON-INVASIVE SENSOR

(71) Applicant: THE JOHNS HOPKINS UNIVERSITY, Baltimore, MD (US)

(72) Inventors: Suchi Saria, New York, NY (US); Andy Jinhua Ma, Baltimore, MD (US); Austin Reiter, Severna Park, MD (US)

(73) Assignee: The Johns Hopkins University, Baltimore, MD (US)

(*) Notice: Subject to any disclaimer, the term of this patent is extended or adjusted under 35 U.S.C. 154(b) by 895 days.

(21) Appl. No.: 16/339,152

(22) PCT Filed: Oct. 4, 2017

(86) PCT No.: PCT/US2017/055108
§ 371 (c)(1),
(2) Date: Apr. 3, 2019

(87) PCT Pub. No.: WO2018/067684
PCT Pub. Date: Apr. 12, 2018

(65) Prior Publication Data
US 2019/0231231 A1    Aug. 1, 2019

Related U.S. Application Data

(60) Provisional application No. 62/403,890, filed on Oct. 4, 2016.

(51) Int. Cl.
*A61B 5/1171*    (2016.01)
*G06T 7/215*    (2017.01)
(Continued)

(52) U.S. Cl.
CPC .......... *A61B 5/1128* (2013.01); *A61B 5/1115* (2013.01); *A61B 5/1116* (2013.01);
(Continued)

(58) Field of Classification Search
None
See application file for complete search history.

(56) References Cited

U.S. PATENT DOCUMENTS

2012/0075464 A1* 3/2012 Derenne .............. A61B 5/0036
600/595
2015/0109442 A1    4/2015 Derenne et al.

* cited by examiner

*Primary Examiner* — Idowu O Osifade

(57) ABSTRACT

An embodiment in accordance with the present invention includes a technology to continuously measure patient mobility automatically, using sensors that capture color and depth images along with algorithms that process the data and analyze the activities of the patients and providers to assess the highest level of mobility of the patient. An algorithm according to the present invention employs the following five steps: 1) analyze individual images to locate the regions containing every person in the scene (Person Localization), 2) for each person region, assign an identity to distinguish 'patient' vs. 'not patient' (Patient Identification), 3) determine the pose of the patient, with the help of contextual information (Patient Pose Classification and Context Detection), 4) measure the degree of motion of the patient (Motion Analysis), and 5) infer the highest mobility level of the patient using the combination of pose and motion characteristics (Mobility Classification).

20 Claims, 8 Drawing Sheets

(51) Int. Cl.
*G16H 30/40* (2018.01)
*A61B 5/11* (2006.01)
*G08B 21/04* (2006.01)
*G16H 30/20* (2018.01)
*G16H 40/63* (2018.01)
*G06V 40/20* (2022.01)
*G06V 40/10* (2022.01)
*G06T 7/00* (2017.01)

(52) U.S. Cl.
CPC ........... *A61B 5/1118* (2013.01); *A61B 5/1171* (2016.02); *G06T 7/0012* (2013.01); *G06T 7/215* (2017.01); *G06V 40/103* (2022.01); *G06V 40/25* (2022.01); *G08B 21/04* (2013.01); *G08B 21/043* (2013.01); *G08B 21/0415* (2013.01); *G08B 21/0476* (2013.01); *G16H 30/20* (2018.01); *G16H 30/40* (2018.01); *G16H 40/63* (2018.01)

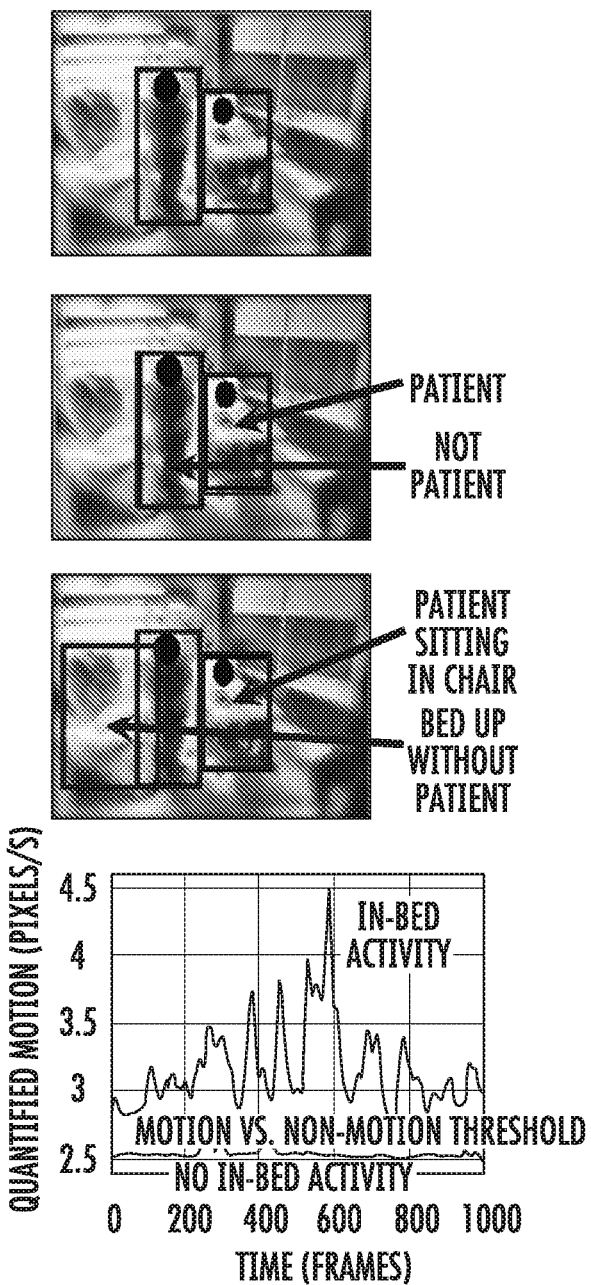
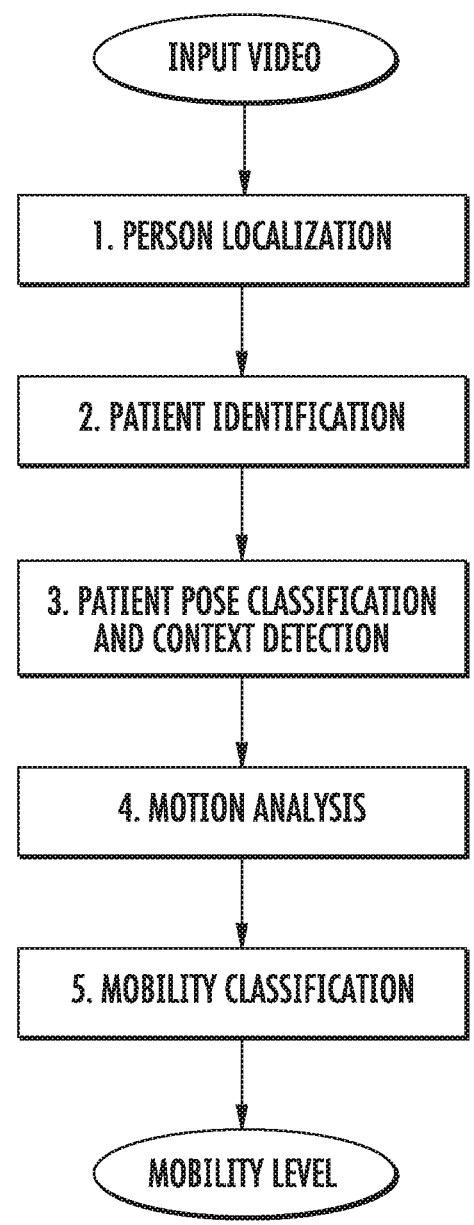
FIG. 6A                    FIG. 6B

MEASURING PATIENT MOBILITY IN THE ICU USING A NOVEL NON-INVASIVE SENSOR

CROSS-REFERENCE TO RELATED APPLICATIONS

This application is a 35 U.S.C. § 371 U.S. national entry of International Application PCT/US2017/055108, having an international filing date of Oct. 4, 2017, which claims the benefit of U.S. Provisional Application No. 62/403,890, filed Oct. 4, 2016, the content of each of the aforementioned applications is herein incorporated by reference in their entirety.

FIELD OF THE INVENTION

The present invention relates generally to image-based medical informatics. More particularly, the present invention relates to measuring patient mobility in the ICU using a novel non-invasive sensor.

BACKGROUND OF THE INVENTION

Monitoring human activities in complex environments are finding an increase in interest. In 2012, the Institute of Medicine released their landmark report on developing digital infrastructures that enable rapid learning health systems; one of their key postulates is the need for improvement technologies for measuring the care environment. Currently, simple measures such as whether the patient has moved in the last 24 hours, or whether the patient has gone unattended for several hours require manual observation by a nurse, which is highly impractical to scale. Early mobilization of critically ill patients has been shown to reduce physical impairments and decrease length of stay, however the reliance on direct observation limits the amount of data that may be collected. Accurate measurement of patient mobility, as part of routine care, assists in evaluating early mobilization and rehabilitation and helps to understand patient exposure to the harmful effects of bedrest.

To automate this process, non-invasive low-cost camera systems have begun to show promise, though current approaches are limited due to the unique challenges common to complex environments. First, though person detection in images is an active research area, significant occlusions present limitations, because the expected appearances of people do not match what is observed in the scene. Part-based deformable methods do somewhat address these issues as well as provide support for articulation, however when combining deformation with occlusion, these too suffer for similar reasons.

In research, patient mobility measurement may be performed via direct observation by a trained and dedicated researcher. Direct observation techniques, such as behavioral mapping, provide comprehensive descriptive data sets and are more accurate than retrospective report, but are labor-intensive, thus limiting the amount and duration of data collection. If evaluated as part of routine clinical care, mobility status is typically estimated using a mobility scale and recorded once or twice daily. However, such discrete subjective recordings of a patient's maximal level of mobility over a 12 or 24 hour time period are subject to recall bias and not truly representative of a patient's overall mobility level (e.g., a patient may achieve a maximal mobility level, such as standing, only for a couple of minutes in a day). Thus, accurate manual measurement and recording of mobility level is not feasible for whole-day observation.

Currently, few techniques exist to automatically and accurately monitor ICU patient's mobility. Accelerometry is one method that has been validated, but it has limited use in critically ill inpatient populations. Related to multi-person tracking, methods have been introduced to leverage temporal cues, however hand-annotated regions are typically required at the onset, limiting automation. To avoid manual initializations, techniques such as employ a single per-frame detector with temporal constraints. Because single detectors are limited towards appearance variations, proposes to make use of multiple detectors, however this assumes that the spatial configuration between the detectors is fixed, which does not scale to address significant pose variations.

Much activity analysis research has approached action classification with bag-of-words approaches. Typically, spatio-temporal features, such as Dense Trajectories, are used with a histogram of dictionary elements or a Fisher Vector encoding. Recent work has applied Convolutional Neural Network (CNN) models to the video domain by utilizing both spatial and temporal information within the network topology. Other work uses Recurrent Neural Networks with Long Short Term Memory to model sequences over time.

Accordingly, there is a need in the art for a non-invasive automated approach to measuring patient mobility and care processes due to the advent of inexpensive sensing hardware and low-cost data storage, and the maturation of machine learning and computer vision algorithms for analysis.

SUMMARY OF THE INVENTION

The foregoing needs are met, to a great extent, by the present invention which provides a method of measuring patient mobility within a room including analyzing individual images from a RGB-D sensor to locate a region containing each person in the room. The method includes assigning an identity for each person in the region, to distinguish 'patient' vs. 'not patient'. The method also includes determining a pose of the patient, with contextual information and measuring a degree of motion of the patient. Additionally, the method includes inferring the highest mobility level of the patient using the combination of pose and motion characteristics.

In accordance with an aspect of the present invention, the method includes generating a volumetric representation of patient movement around the room. The method can also include generating a heatmap of patient movement throughout the room and generating a heatmap of movement of regions of the patient's body. The method includes classifying the pose of the patient into 4 discrete categories: (1) lying in bed, (2) sitting in bed, (3) sitting in chair, and (4) standing. The method includes classifying patient motion as "in-bed activity" if the patient's total body speed signature exceeds a threshold. Additionally, the method includes classifying patient motion as "nothing in bed" if the patient's total body speed signature is below a threshold. The method includes executing the method with a non-transitory computer readable medium. The method also includes a predetermined area for measuring patient mobility and defining the predetermined area for measuring patient mobility as the patient room.

In accordance with another aspect of the present invention, a system for measuring patient mobility within a room includes an RGB-D sensor. The system also includes a non-transitory computer readable medium programmed for analyzing individual images from the RGB-D sensor to locate a region containing each person in the room. The non-transitory computer readable medium is programmed for assigning an identity for each person in the region, to distinguish 'patient' vs. 'not patient' and determining a pose of the patient, with contextual information. Additionally, the non-transitory computer readable medium is programmed for measuring a degree of motion of the patient and inferring the highest mobility level of the patient using the combination of pose and motion characteristics.

In accordance with still another aspect of the present invention, the system includes generating a volumetric representation of patient movement. The system includes generating a heatmap of patient movement and generating a heatmap of movement of regions of the patient's body. The system includes classifying the pose of the patient into 4 discrete categories: (1) lying in bed, (2) sitting in bed, (3) sitting in chair, and (4) standing. Additionally, the system includes classifying patient motion as "in-bed activity" if the patient's total body speed signature exceeds a threshold. The system includes classifying patient motion as "nothing in bed" if the patient's total body speed signature is below a threshold. The system includes assigning a numerical mobility value to the patient mobility. The system includes defining a predetermined area for measuring patient mobility and defining the predetermined area for measuring patient mobility as the patient room.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIG. 6A illustrates graphical views of patient mobility and image views from a patient room according to an embodiment of the present invention.

FIG. 6B illustrates a flow diagram view of an algorithm according to an embodiment of the present invention.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention includes a system to continuously measure patient mobility automatically, using sensors that capture color and depth image data. The system also processes the color and depth image data to analyze the activities of the patients and providers to assess the highest level of mobility of the patient. Analysis according to the present invention employs the following five steps: 1) analyze individual images to locate the regions containing every person in the scene (Person Localization), 2) for each person region, assign an identity to distinguish 'patient' vs. 'not patient' (Patient Identification), 3) determine the pose of the patient, with the help of contextual information (Patient Pose Classification and Context Detection), 4) measure the degree of motion of the patient (Motion Analysis), and 5) infer the highest mobility level of the patient using the combination of pose and motion characteristics (Mobility Classification).

Figure 1:
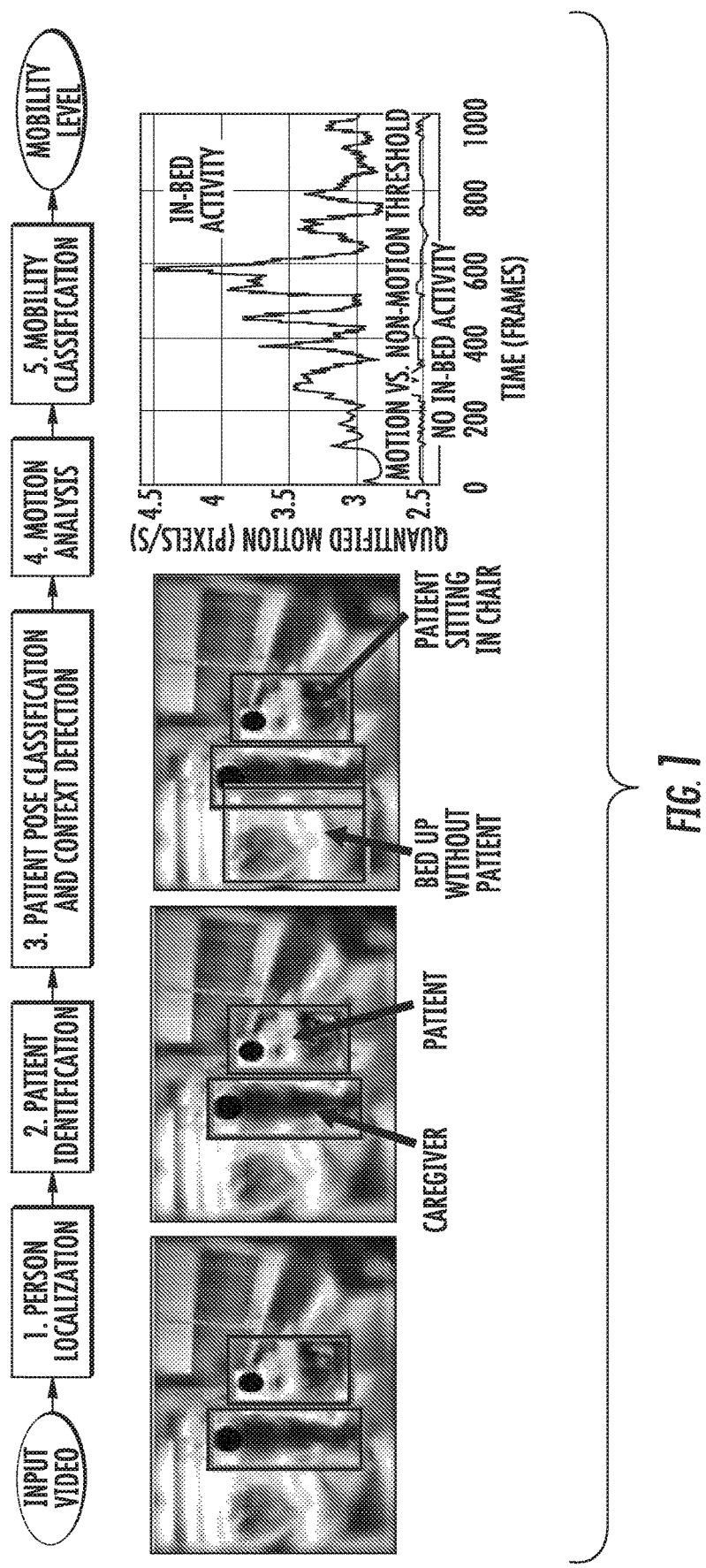
FIG. 1 illustrates a flowchart of mobility prediction framework, according to an embodiment of the present invention.

FIG. 1 shows an overview of a system of the present invention. People are localized, tracked, and identified within a predetermined space using an RGB-D sensor. The predetermined space can be a room, a region of a room, or other space where tracking may be useful. The parameters can be walls of the room or dimensions entered into the system to define the tracking area. FIG. 1 illustrates a flowchart of mobility prediction framework, according to an embodiment of the present invention. The system tracks people in the patient's room, identifies the "role" of each ("patient", "caregiver", or "family member"), relevant objects, and builds attribute features for mobility classification. The present invention predicts the pose of the patient and identifies nearby objects within the predetermined space to serve as context. Finally, in-place motion is analyzed and a classifier trained to determine the highest level of patient mobility.

Figures 2A, 2B, 2C, 2D:
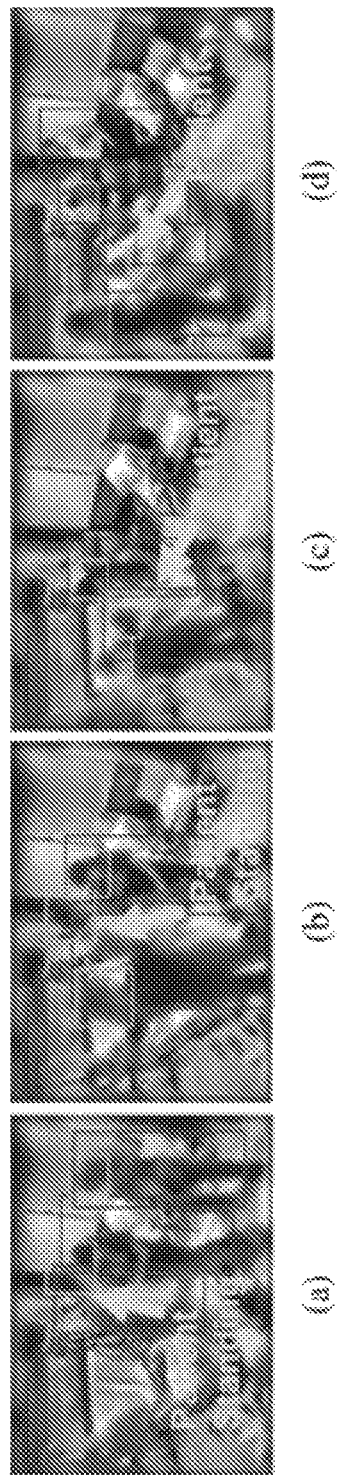
FIGS. 2A-2D illustrate image views from full-body and Head detectors.

The tracking method works by formulating an energy function having spatial and temporal consistency over multiple part-based detectors (see FIGS. 2A-2D). FIGS. 2A-2D illustrate image views from full-body and Head detectors. The head detector may fail with proximity or distance, as illustrated in FIGS. 2A and 2D, respectively. The full-body detector may also struggle with proximity, as illustrated in FIGS. 2B and 2C, respectively. (To protect privacy, all images are blurred).

The relationship between detectors within a single frame is modeled using a deformable spatial model and then tracked in an online setting. Modeling Deformable Spatial Configurations: For objects that exhibit deformation, such as humans, there is an expected spatial structure between regions of interest (ROIs) (e.g., head, hands, etc.) across pose variations. Within each pose (e.g. lying, sitting, or standing), an ROI (e.g. head) can be estimated based on other ROIs (e.g. full-body). To model such relationships, there is a projection matrix $A_{ll'}^c$, which maps the location of ROI l to that of $l_0$ for a given pose c. With a training dataset, C types of poses are determined automatically by clustering location features, and projection matrix $A_{ll'}^c$ can be learnt by solving a regularized least-square optimization problem.

To derive the energy function of the deformable model, the number of persons in the t-th frame is denoted as $M^t$. For the m-th person, the set of corresponding bounding boxes from L ROIs is defined by $X^t = \{X_1^t(m), \ldots, X_L^t(m)\}$. For any two proposed bounding boxes $X_l^t(m)$ and $X_{l'}^t(m)$ at frame t for individual m, the deviation from the expected spatial configuration is quantified as the error between the expected location of the bounding box for the second ROI conditioned on the first. The total cost is computed by summing, for each of the $M^t$ individuals, the minimum cost for each of the C subcategories:

$$E_{spa}(X^t, M^t) = \sum_{m=1}^{M^t} \min_{1 \leq c \leq C} \Sigma_{l \neq l'} \|A_{ll'}^c X_l^t(m) - X_{l'}^t(m)\|^2 \quad (1)$$

Grouping Multiple Detectors:

The process of detecting people to track is automated using a combination of multiple part-based detectors. A collection of existing detection methods can be employed to train K detectors; each detector is geared towards detecting an ROI. Let us consider two bounding boxes $D_k^t(n)$ and $D_{k'}^t(n')$ from any two detectors k and k', respectively. If these are from the same person, the overlapped region is large when they are projected to the same ROI using a projection matrix. In this case, the average depths in these two bounding boxes are similar. The probability that these are from the same person is calculated as:

$$p = a p_{over} + (1-a) p_{depth} \quad (2)$$

where a is a positive weight, $p_{over}$ and $p_{depth}$ measure the overlapping ratio and depth similarity between two bounding boxes, respectively. These scores are $$p_{over} = \left( \frac{|A_{l(k)l(k')}^c D_k^t(n) \cap D_{k'}^t(n')|}{\min(|A_{l(k)l(k')}^c D_k^t(n)|, |D_{k'}^t(n')|)}, \frac{|D_k^t(n) \cap A_{l(k)l(k)}^c D_{k'}^t(n')|}{\min(|D_k^t(n)|, |A_{l(k)l(k)}^c D_{k'}^t(n')|)} \right) \quad (3)$$

$$p_{depth} = \frac{1}{2} e^{-\frac{(v_k^t(n) - v_{k'}^t(n'))^2}{2\sigma_k^t(n)^2}} + \frac{1}{2} e^{-\frac{(v_k^t(n) - v_{k'}^t(n'))^2}{2v_{k'}^t(n')^2}} \quad (4)$$

where l maps the k-th detector to the l-th region-of-interest, v and 6 denote the mean and standard deviation of the depth inside a bounding box, respectively.

By the proximity measure given by (2), the detection outputs are grouped into $N^t$ sets of bounding boxes. In each group $G^t(n)$, the bounding boxes are likely from the same person. Then, a cost function that represents the matching relationships between the true positions of the tracker and the candidate locations suggested by the individual detectors are defined as:

$$E_{det}(X^t, M^t) = \sum_{n=1}^{N^t} \min_{1 \leq m \leq M^t} \sum_{D_k^t(n') \in G^t(n)} w_k^t(n) \|D_k^t(n') - X_{l(k)}^t(m)\|^2 \quad (5)$$

where $w_k^t(n)$ is the detection score as a penalty for each detected bounding box. Tracking Framework: The tracker is initialized at time t=1 by aggregating the spatial (Eq. 1) and detection matching (Eq. 5) cost functions. To determine the best bounding box locations at time t conditioned on the inferred bounding box locations at time t−1, the temporal trajectory $E_{dyn}$ and appearance $E_{app}$ energy functions are extended and the joint optimization solved as:

$$\min_{X^t, M^t} \lambda_{det} E_{det} + \lambda_{spa} E_{spa} + \lambda_{exc} E_{exc} + \lambda_{reg} E_{reg} + \lambda_{dyn} E_{dyn} + \lambda_{app} E_{app} \quad (6)$$

TABLE 1

| Sensor Scale | ICU Mobility Scale[10] | Sensor Label |
|---|---|---|
| A. Nothing in bed | 0. Nothing, lying in bed (i) | i |
| B. In-bed activity | 1. Sitting in bed (ii), exercises in bed (iii) | ii<br>iii |
| C. Out-of-bed activity | 2. Passively moved to chair (no standing) | iii→v/<br>vii→iv |
|  | 3. Sitting over edge of bed (iv) | iv |
|  | 4. Standing (v) | v |
|  | 5. Transferring bed to chair (with standing) | iii→v/<br>vii→iv |
|  | 6. Marching (vi) in place (at bedside) for short duration | vi |
| D. Walking (vii) | 7. Walking with assistance of 2 or more people | vii |
|  | 8. Walking with assistance of 1 person |  |
|  | 9. Walking independently with a gait aid |  |
|  | 10. Walking independently without a gait aid |  |

Table 1.

Table comparing the Sensor Scale, containing the 4 discrete levels of mobility that the present invention is trained to categorize from a video clip of a patient in the ICU, to the standardized ICU Mobility Scale, used by clinicians in practice today.

Patient Identification:

A pre-trained CNN is fine-tuned, which is initially trained on ImageNet (http://image-net.org/). From the RGB-D sensor, the color images are used to classify images of people into one of the following categories: patient, caregiver, or family-member. Given each track from the multi-person tracker, a small image is extracted according to the tracked bounding box to be classified. By understanding the role of each person, the activity analysis is tuned to focus on the patient as the primary "actor" in the scene and utilize the caregivers into supplementary roles.

Patient Pose Classification and Context Detection:

Next, the pose of the patient is estimated, and so a pre-trained network is fine-tuned to classify the depth images into one of the following categories: lying-down, sitting, or standing. Depth is prioritized over color as this is a geometric decision. To supplement the final representation, a real-time object detector is applied to localize important objects that supplement the state of the patient, such as: bed upright, bed down, and chair. By combining bounding boxes identified as people with bounding boxes of objects, the present invention may better ascertain if a patient is, for example, "lying-down in a bed down" or "sitting in a chair".

Motion Analysis:

Finally, in-place body motion is computed. For example, if a patient is lying in-bed for a significant period of time, clinicians are interested in how much exercise in-bed occurs. To achieve this, the mean magnitude of motion is computed with a dense optical flow field within the bounding box of the tracked patient between successive frames in the sequence. This statistic indicates how much frame-to-frame, in-place motion the patient is exhibiting.

Mobility Classification:

Table 1 describes a clinically-accepted 11-point mobility scale (ICU Mobility Scale). This is collapsed into the Sensor Scale (left) of 4 discrete categories. The motivation for this collapse was that when a patient walks, this is often performed outside the room where the sensors cannot see.

By aggregating the different sources of information described in the preceding steps, attribute feature $F_t$ is constructed with: 1. Was a patient detected in the image? (0 for no; 1 for yes); 2. What was the patient's pose? (0 for sitting; 1 for standing; 2 for lying-down; 3 for no patient found); 3. Was a chair found? (0 for no; 1 for yes); 4. Was the patient in a bed? (0 for no; 1 for yes); 5. Was the patient in a chair? (0 for no; 1 for yes); 6. Average patient motion value; 7. Number of caregivers present in the scene.

These attributes were chosen because their combination describes the "state" of the activity. Given a video segment of length T, all attributes $F=[F_1, F_2, \ldots, F_T]$ are extracted and the mean $F_\mu = \Sigma_{t=1}^{T} = F_t/T$ is used to represent the overall video segment (the mean is used to account for spurious errors that may occur). A Support Vector Machine (SVM) is trained to automatically map each $F\mu$ to the corresponding Sensor Scale mobility level from Table 1.

Figure 3:
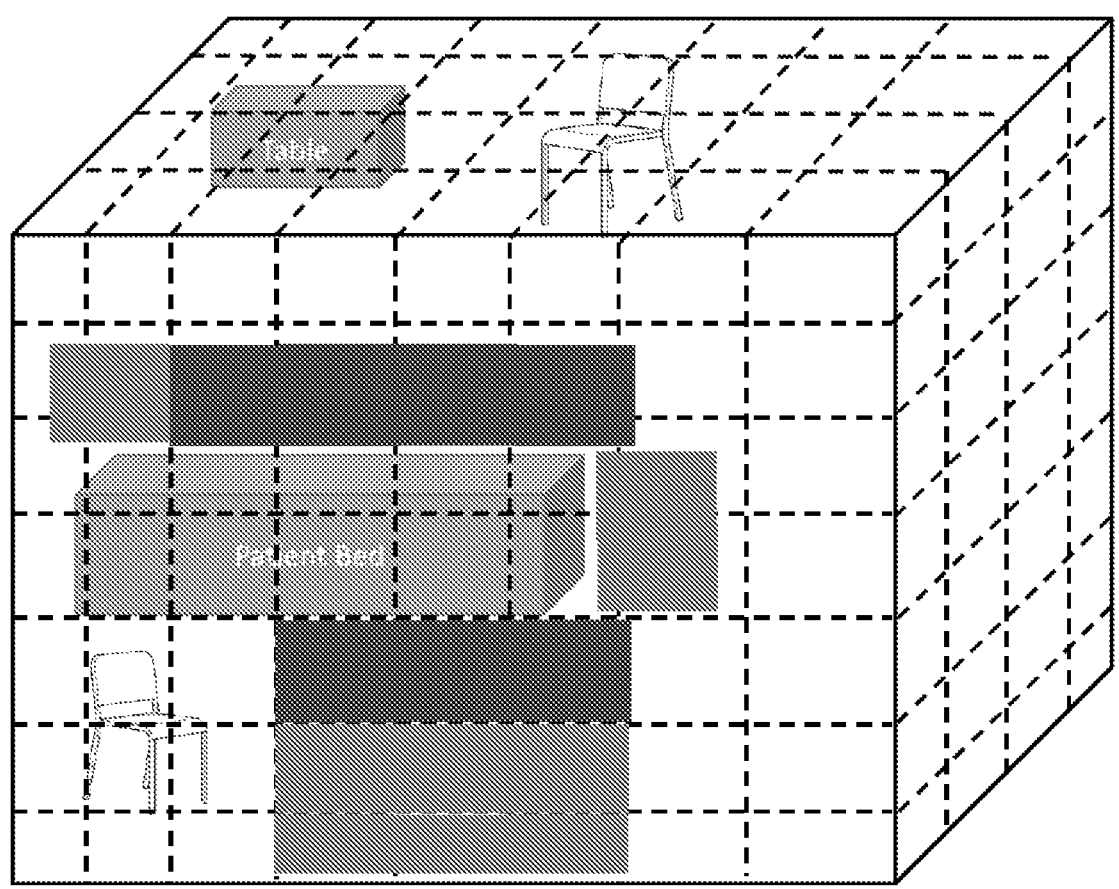
FIG. 3 illustrates a three-dimensional view of a patient room with a heatmap of movement within the room, according to an embodiment of the present invention. In another representation of the data, an overhead view is provided to show movement throughout the patient room.
Figure 4:
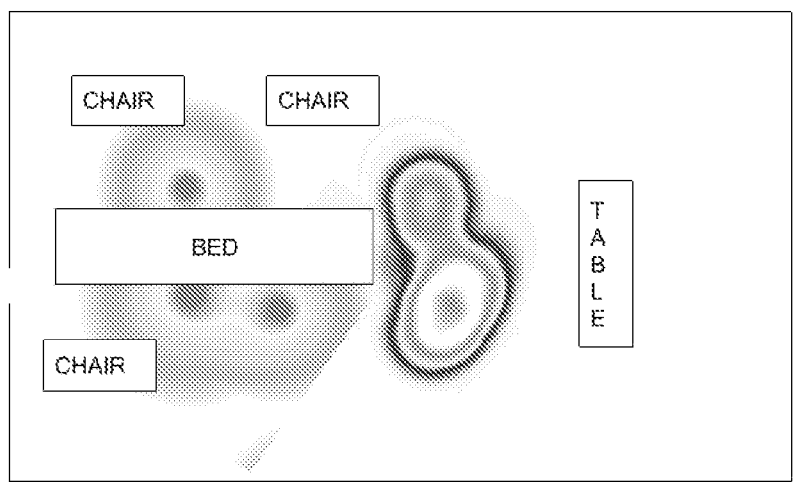
FIG. 4 illustrates a top down view of a patient room with a heatmap of movement within the room, according to an embodiment of the present invention.

For healthcare provider assessment of patient mobility, the data gathered and analyzed can be transformed and presented in a number of ways. For example, visual representations of the room from the RGB-D can be overlayed with heat maps of patient activity. One such representation of the data is a volumetric representation tracking people throughout the patient room, as illustrated in FIG. 3. FIG. 3 illustrates a three-dimensional view of a patient room with a heatmap of movement within the room, according to an embodiment of the present invention. In another representation of the data, an overhead view is provided to show movement throughout the patient room. FIG. 4 illustrates a top down view of a patient room with a heatmap of movement within the room, according to an embodiment of the present invention. Other transformations and representations of the data are also included within the scope of the present invention. Examples include heatmaps of patient movement within the room or on a visual representation of the patient's body to show movement of specific body parts/areas of the patient, volumetric representations can also include layers of patient movement over a timeline of hours or days. Another example includes an image of the room labeled with patient activities that occurred in different areas of the room. These examples are not meant to be considered limiting, and any visual representation of the data known to or conceivable to one of skill in the art is included.

EXAMPLES

Figure 5:
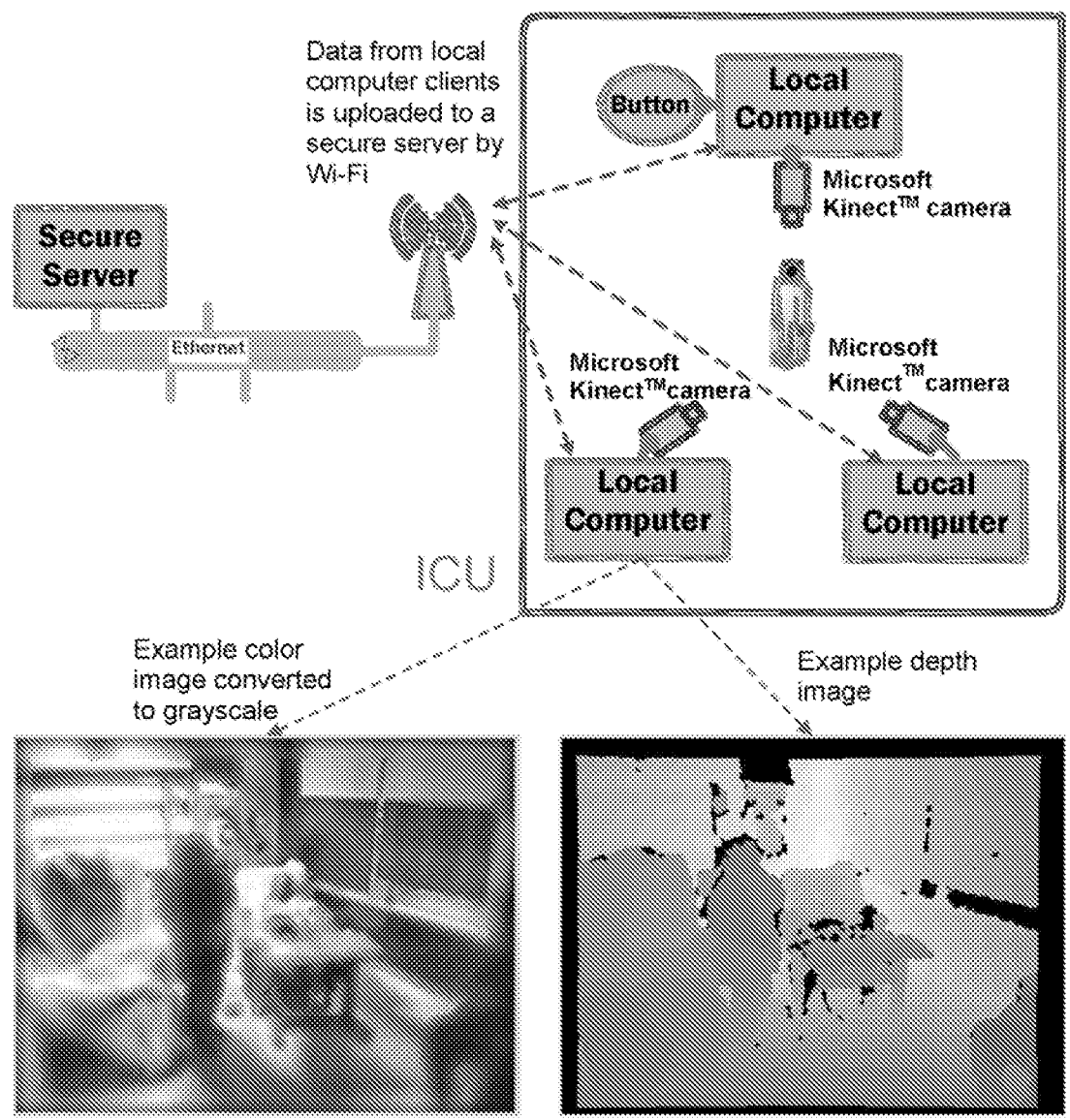
FIG. 5 illustrates a sensor system, according to an embodiment of the present invention in an ICU room and example color (converted to grayscale for demonstration) and depth images captured by the sensors.

Several exemplary implementations of the present invention are included, in order to further illustrate the invention. These examples are included merely as illustrations of the present invention, and are not to be considered limiting. While implementation is contemplated in the ICU, this is not to be considered limiting. The invention can be implemented in any space where mobility tracking is needed. In one exemplary implementation of the present invention, data were collected with three RGB-D sensors mounted on the walls of a single private patient room in the ICU to permit views of the entire room without obstructing clinical activities, as illustrated in FIG. 5. FIG. 5 illustrates a sensor system, according to an embodiment of the present invention in an ICU room and example color (converted to grayscale for demonstration) and depth images captured by the sensors. The grayscale image on the left provides texture information for human/object detection. Faces are obscured and the image is blurred for identity protection. The depth image on the right shows the distance from the camera to the human/object with darker gray pixels indicating areas closer to the camera, lighter gray pixels indicating areas farther away and black pixels indicating that the depth camera cannot capture the distance values around those regions. The depth image provides complementary information for better human/object detection.

The sensors were activated and continuously captured color and depth image data from the time of patient consent until ICU discharge. Example color (converted to grayscale for demonstration) and depth images obtained from the sensor are shown in FIG. 5. Each sensor was connected to a dedicated encrypted computer containing a storage drive. The data were de-identified at the local storage drive, and then transferred, using a secure encrypted protocol, to the server for a second level of obfuscation, storage and analysis.

The present invention automatically analyzes the sensor color and depth image data to measure patient mobility and assign the highest level of mobility within a time period. To characterize the highest level of mobility numerically, a validated 11-point mobility scale was collapsed into the 4 mutually exclusive mobility categories of Table 2. Walking categories were collapsed because the sensor only measures movement within the ICU room. As such, if a patient walks, then this is often performed outside of the room. The remaining categories were collapsed because the data set, though it included a significant number of hours of sensed data, did not include a sufficient number of mobility events specific to each discrete mobility categories in the 11-point scale.

362 hours of sensor color and depth image data were recorded and curated into 109 segments, each containing 1000 images, from 8 patients. These segments were specifically sampled to ensure representation of each of the mobility levels. Of the 109 segments, the present invention was developed using 26 of these from 3 ICU patients ("development data") and validated on 83 of the remainder segments obtained from 5 different ICU patients ("validation data").

The algorithmic procedures performed for mobility measurement, with respect to the present example are shown in FIG. 6B and described below. FIG. 6A illustrates images from a patient room according to an embodiment of the present invention. The images of FIG. 6A include overlaid bounding boxes to indicate the positions of people in the patient room as detected by the sensor. The flow chart of FIG. 6B shows the stages of the algorithm of the present invention.

The algorithm employs the following five steps: 1) analyze individual images to locate the regions containing every person in the scene (Person Localization), 2) for each person region, assign an identity to distinguish 'patient' vs. 'not patient' (Patient Identification), 3) determine the pose of the patient, with the help of contextual information (Patient Pose Classification and Context Detection), 4) measure the degree of motion of the patient (Motion Analysis), and 5) infer the highest mobility level of the patient using the combination of pose and motion characteristics (Mobility Classification).

The present invention was developed using "bounding boxes" of people and objects in the development data (FIG. 6A). A bounding box is defined as a region of an image containing a person or object. For the development data, a researcher annotated for who the people were in each image (patient vs. not-patient) as well as where objects were located (bed or chair). Using these annotations, the present invention was trained to automate each of the 5 steps described below.

Given a segment of images, each image was analyzed independently and in order. For each image, the present invention identified all regions containing persons using three steps. First, a collection of person-detection algorithms was used to identify candidate locations for persons in each image. Second, these outputs were combined to obtain the high likelihood locations. Finally, false detections are further removed by imposing consistency checks for locations found in consecutive images. The result of this step was bounding boxes around persons in the image (FIG. 6A).

Next, for all persons identified in an image, the present invention determined whether they are a 'patient' or 'not patient' (e.g. caregiver or family member). This was done via a Convolutional Neural Network (CNN) algorithm. A CNN is a machine learning algorithm that can be trained to classify inputs into a specific class of outputs (e.g., image regions into person vs. not), and then given a bounded region of a person, the algorithm can automatically determine whether or not they are a patient (FIG. 6B). The CNN achieves this automatically through learning characteristics of people's appearance based on color and geometry.

Once both location and identity of the people in each image were established, next their pose was characterized for the purpose of mobility labeling. Poses were classified into 4 discrete categories: (1) lying in bed, (2) sitting in bed, (3) sitting in chair, and (4) standing. A pose detector was trained using the CNN algorithm that automatically learned the pose of a person. Using annotations from the development data, the CNN was trained to determine if a bounded region of an image contained a person who was "lying-down", "sitting", or "standing". Besides pose, an object detection algorithm was used to automatically locate the bounded regions of objects in the images that correspond to "beds" and "chairs" (also called "object detections"). These were then combined to the get the patient's overall pose (FIG. 6A and FIG. 6B).

After classifying the pose and context of a person identified as patient, information about their movement was extracted by analyzing consecutive images to measure motion. Specifically, for a bounding region containing a person in a given image, the subsequent images in the segment were analyzed within the same region and measured the mean and variance of the changes in image intensity per pixel. In addition, speed of movement was computed by measuring the total distance that the person moved (as measured by the center of the bounding regions) divided by the duration over which the movement was made (FIG. 6A and FIG. 6B).

In this final step, the information related to pose, context, and motion computed in the steps above was aggregated into a series of numbers (often termed "feature") to determine the final mobility level according to the scale in Table 2. The feature contained the following values: 1) was a patient detected in the image?; 2) what was the patient's pose?; 3) was a chair found?; 4) was the patient in a bed?; 5) was the patient in a chair?; 6) what was the average patient motion value?; and 7) how many caregivers were present in the room? These features were used to train a Support Vector Machine (SVM) classifier to automatically map each feature to the corresponding mobility level from Table 2.

TABLE 2

| Characteristics | N = 3 (development) | N = 5 (validation) |
| --- | --- | --- |
| Age (y), Median (IQR) | 67 (60-71) | 67 (52-77) |
| Male | 1 (33%) | 2 (40%) |
| ICU length of stay (d), Median (IQR) | 5 (1-5) | 3 (2-5) |
| Type of Surgery | | |
| Endocrine (Pancreatic) | 1 | 1 |
| Gastrointestinal | 1 | 2 |
| Gynecologic | 1 | |
| Thoracic | | 1 |
| Orthopedics | | 1 |
| APACHE II score, Median (IQR) | 13 (12-28) | 16 (10-21) |

The validation data consisted of 83 segments from 5 patients. This sample size was considered to be sufficient with a 5.22% margin-of-error. For validation, two junior and one senior physician independently reviewed the same segments and were blinded to the evaluation method of present invention, reporting the highest level of patient mobility visualized during each segment, according to the sensor scale (Table 2). In the 27% of visualizations exhibiting disagreement, these were re-reviewed and the majority opinion was considered as the gold standard annotation.

The performance of the present invention was assessed using a weighted Kappa statistic that measured disagreement between the mobility level output of the present invention and the gold standard annotation. A standard linear weighting scheme was applied which penalized according to the number of levels of disagreement (e.g., predicting "A" when expecting "B" yielded a 33% weight on the error whereas a prediction of "A" when expecting "C" yielded a 67% weight on the error, and 100% weight when expecting "D"). The percentage of segments on which the present invention agreed with the gold standard annotation was calculated. The weighted percent observed agreement was computed by one minus the linear weighting of different levels of disagreement. A contingency table was created to report the inter-rater agreement for each mobility level.

Patient demographics for the exemplary implementation are detailed in Table 3. The number of segments annotated as each mobility level, as identified by the physicians (gold standard), is 21 (25%) for "nothing in bed", 30 (36%) for "in-bed activity", 27 (33%) for "out-of-bed activity", and 5 (6.0%) for "walking". Table 4 reports gold standard versus the present invention agreement for each mobility level. In 72 (87%) of the 83 segments there was perfect agreement between the gold standard and the automated score of the present invention. Of the 11 discrepancies, 7 were due to confusion between "nothing in bed" and "in-bed activity". The weighted percent observed agreement was 96%, with a weighted Kappa of 0.86 (95% confidence interval: 0.72, 1.00).

TABLE 3

|  |  | Physician Score | | | | |
| --- | --- | --- | --- | --- | --- | --- |
|  |  | A. Nothing | B. In-bed | C. Out-of-bed | D. Walking | Total |
| Sensor Score | A. Nothing | 18 (22%) | 4 (5%) | 0 | 0 | 22 (27%) |
|  | B. In-bed | 3 (4%) | 25 (30%) | 2 (2%) | 0 | 30 (36%) |
|  | C. Out-of-bed | 0 | 1 (1%) | 25 (30%) | 1 (1%) | 27 (32%) |
|  | D. Walking | 0 | 0 | 0 | 4 (5%) | 4 (5%) |
|  | Total | 21 (26%) | 30 (36%) | 27 (32%) | 5 (6%) | 83 (100%) |

TABLE 4

| Patient Motion Status | Pose | Object | Motion |
| --- | --- | --- | --- |
| i. Lying in bed without motion | Lying | Bed down | No |
| ii. Lying in bed with motion | Lying | Bed down | yes |
| iii. Sitting in bed | Sitting | Bed upright | N/A |
| iv. Sitting in chair | Sitting | Chair | N/A |
| v. Standing without motion | Standing | N/A | No |
| vi. Standing with motion | Standing | N/A | Yes but no moving |
| vii. Walking | Standing | N/A | Yes moving |

Figure 7:
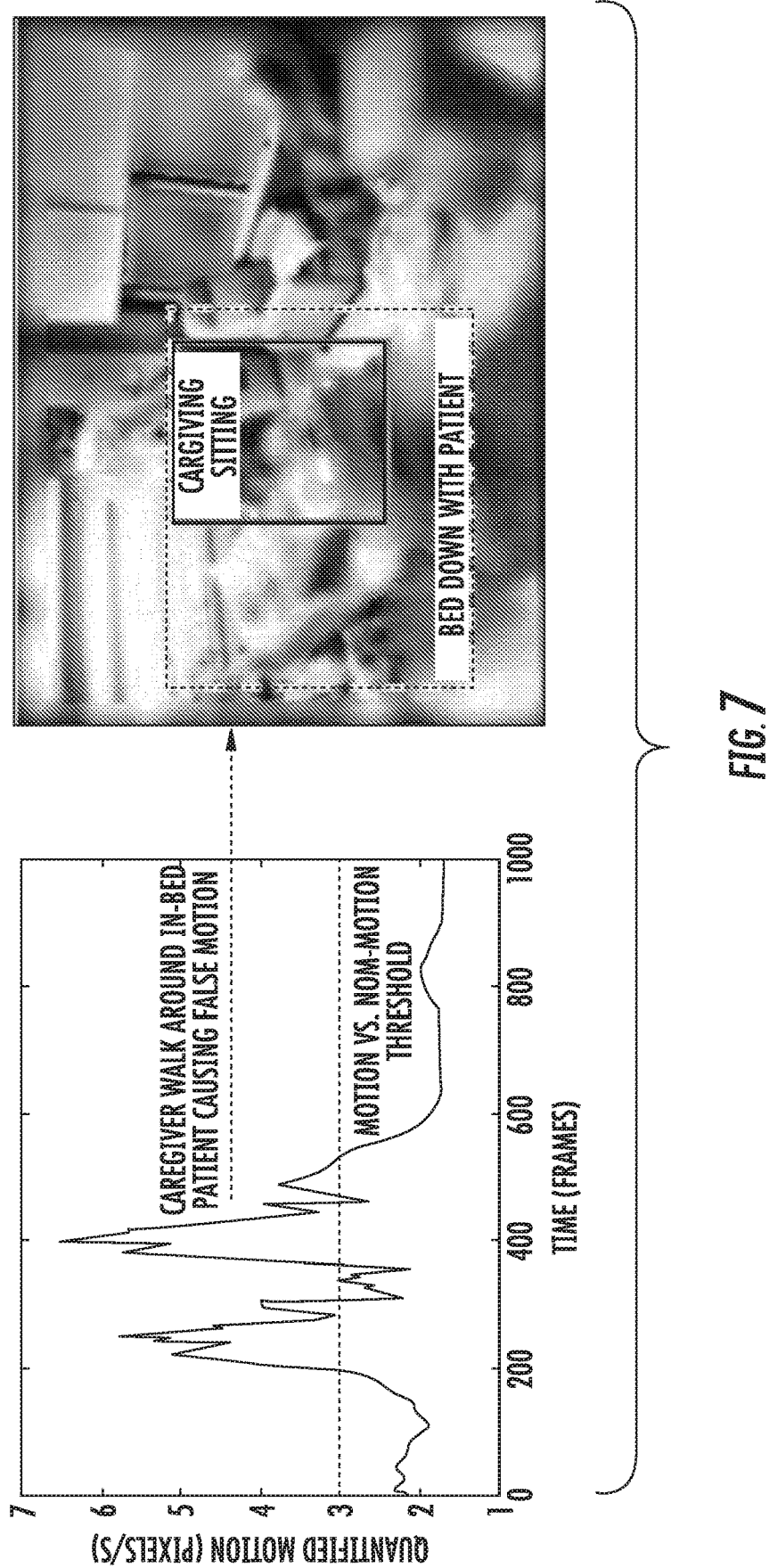
FIG. 7 illustrates graphical and image views of how the present invention can incorrectly measure a patient's mobility when the caregiver is close to the patient.

The main source of difference in sensor and clinician agreement lies in differentiating "nothing in bed" from "in-bed activity". The difference was due, in large part, to segments where the patient motion was subtle. When applying the physician-evaluated discrete scale to the sensor, if the patient's total body speed signature exceeds a threshold, then the sensor labels this mobility level as "in-bed activity". Below this threshold, any body activity is labeled as "nothing in bed". The clinician's activity threshold, which differentiates "nothing in bed" from "in-bed activity", is subjective and different from that of the sensor, which is quantitative and thus more reproducible. Some of these were challenging segments; therefore, these speed judgment discrepancies are not necessarily sensor errors. The sensor rarely exhibited genuine errors due to incorrect assessment of pose or confusing patient identities with provider identities, as illustrated in FIG. 7. FIG. 7 illustrates graphical and image views of how the present invention can incorrectly measure a patient's mobility when the caregiver is close to the patient. Currently, the in-bed motion is measured by image intensity changes in a bounding region containing the patient. This kind of measurement is inaccurate if the bounding region of the caregiver is overlapped with the one of the patient.

Figure 8:
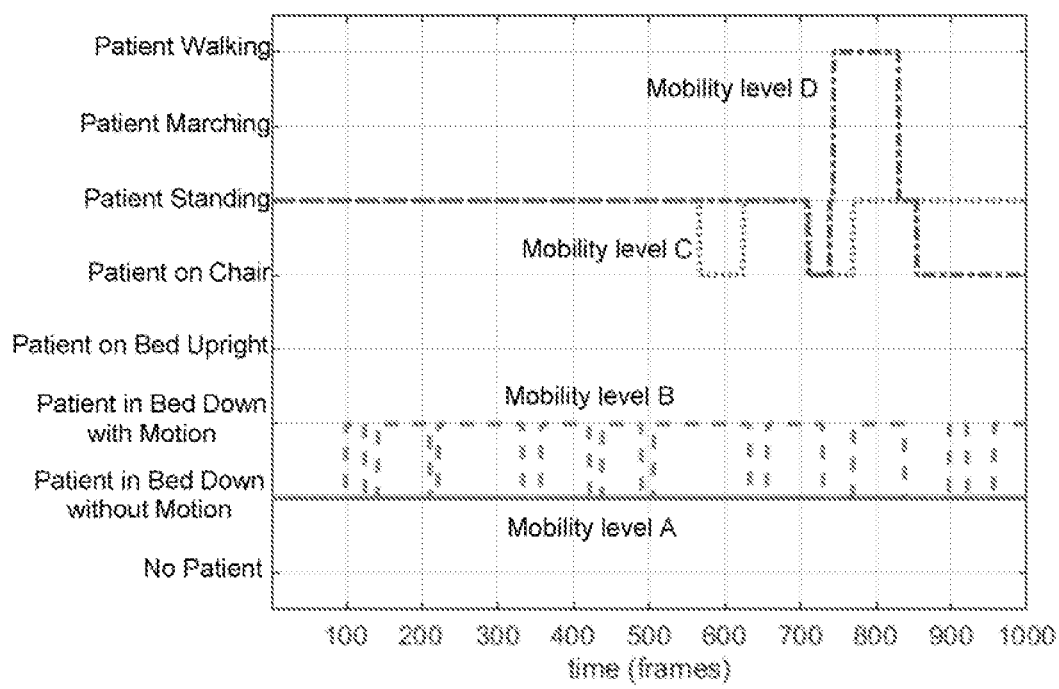
FIG. 8 illustrates a graphical view of how the present invention continuously measures patient mobility.

Patient mobility data derived from the present invention could auto-populate the health record such that providers no longer must subjectively document a highest level of mobility. The present invention could continuously monitor patient mobility in an ICU room and generate and report a single numeric value representing the patient's highest mobility level during an hour's time frame, as illustrated in FIG. 8, as well as more detailed data about specific activity levels and durations. FIG. 8 illustrates a graphical view of how the present invention continuously measures patient mobility. The mobility level for a segment of several images is assigned after analyzing patient motion characteristics over a defined time period. A single numeric value, along with its trend over time is akin to a vital sign, and could be used to stimulate patient mobility quality improvement activities. For example, data from the present invention could be used to provide real-time feedback to providers, patients and their caregivers regarding a patient's mobility status for comparison to a pre-determined activity goal, prompting care changes to ensure that patients are on track to achieving these.

As privacy may pose a concern, family members and providers were reassured by the fact that data was de-identified and encrypted both at the local storage drive and server. They also often expressed comfort with the general presence of sensors given their ubiquity in public areas, expressing gratitude that the sensors were being used to 'do good' and improve the quality of care delivery.

The analysis of the present invention is at the segment level and not at the patient level, and as Table 3 demonstrates, the present invention was exposed to many different variations of human activities from lying motionless in a bed to small motions in bed, sitting up, and walking. Second, though patient and provider privacy was not an issue in the exemplary implementation, further studies are needed to establish the degree of stakeholder comfort with sensing technologies such as those used in this study.

Sensor technology and deep machine learning techniques are used in other industries, but have only recently been explored in health care. The present invention uses inexpensive technology and novel machine learning and computer vision-based algorithms to capture patient mobility in the ICU. The results suggest that new deep learning techniques in machine learning hold promise to automate activity recognition and scene understanding. Other potential applications include delirium assessment (e.g., delirium motoric subtype), patient-provider interaction (e.g., how physicians interact with patients in their room), and evaluation of patient turning in bed (e.g., as part of prevention efforts for pressure ulcers). Adapting these techniques for clinical intervention monitoring offers the potential for improving care measurement and delivery. The next steps include algorithmic refinements, applying the present invention to measure and provide performance feedback to providers and extending the repertoire of clinical tasks.

An accurate method for automating measurement of patient mobility has been developed and evaluated in the ICU using RGB-D sensors, machine learning and computer vision technologies. The present invention addresses a need for effective, inexpensive, continuous evaluation of patient mobility to assist with optimizing patient mobility in the ICU.

The steps and analysis of the present invention can be carried out using a computer, non-transitory computer readable medium, or alternately a computing device or non-transitory computer readable medium incorporated into the imaging device. Indeed, any suitable method of calculation known to or conceivable by one of skill in the art could be used. It should also be noted that while specific equations are detailed herein, variations on these equations can also be derived, and this application includes any such equation known to or conceivable by one of skill in the art. A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape. The computing device can be a special computer designed specifically for this purpose. The computing device can be unique to the present invention and designed specifically to carry out the method of the present invention. The computing device can also take the form of an operating console computer for the imaging device. The operating console is a non-generic computer specifically designed by the imaging device manufacturer for bilateral (input output) communication with the device. It is not a standard business or personal computer that can be purchased at a local store. Additionally this console computer carries out communications with the scanner through the execution of proprietary custom built software that is designed and written by the scanner manufacturer for the computer hardware to specifically operate the scanner hardware.

The many features and advantages of the invention are apparent from the detailed specification, and thus, it is intended by the appended claims to cover all such features and advantages of the invention, which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method of measuring patient mobility comprising:
   analyzing individual images from an RGB-D sensor to locate a region containing each person including a patient;
   assigning an identity for each person in the region, to distinguish 'patient' vs. 'not patient';
   determining a pose of the patient, with contextual information;
   measuring a degree of motion of the patient; and
   inferring a highest mobility level of the patient using the combination of pose and motion characteristics.

2. The method of claim 1 further comprising generating a volumetric representation of patient mobility.

3. The method of claim 1 further comprising generating a heatmap of patient mobility.

4. The method of claim 1 further comprising generating a heatmap of movement of regions of the patient's body.

5. The method of claim 1 further comprising classifying the pose of the patient into 4 discrete categories: (1) lying in bed, (2) sitting in bed, (3) sitting in chair, and (4) standing.

6. The method of claim 1 further comprising classifying patient motion as "in-bed activity" if a total body speed signature of the patient exceeds a threshold.

7. The method of claim 1 further comprising classifying patient motion as "nothing in bed" if a total body speed signature of the patient is below a threshold.

8. The method of claim 1 further comprising executing the method with a non-transitory computer readable medium.

9. The method of claim 1 further comprising defining a predetermined area for measuring patient mobility.

10. The method of claim 9 further comprising defining the predetermined area for measuring patient mobility as the patient room.

11. A system for measuring patient mobility comprising:
    an RGB-D sensor;
    a non-transitory computer readable medium programmed for:
      analyzing individual images from the RGB-D sensor to locate a region containing each person, including the patient;
      assigning an identity for each person in the region, to distinguish 'patient' vs. 'not patient';
      determining a pose of the patient, with contextual information;
      measuring a degree of motion of the patient; and
      inferring the highest mobility level of the patient using the combination of pose and motion characteristics.

12. The system of claim 11 further comprising generating a volumetric representation of patient movement.

13. The system of claim 11 further comprising generating a heatmap of patient movement.

14. The system of claim 11 further comprising generating a heatmap of movement of regions of the patient's body.

15. The system of claim 11 further comprising classifying the pose of the patient into 4 discrete categories: (1) lying in bed, (2) sitting in bed, (3) sitting in chair, and (4) standing.

16. The system of claim 11 further comprising classifying patient motion as "in-bed activity" if a total body speed signature of the patient exceeds a threshold.

17. The system of claim 11 further comprising classifying patient motion as "nothing in bed" if a total body speed signature of the patient is below a threshold.

18. The system of claim 11 further comprising assigning a numerical mobility value to the patient mobility.

19. The system of claim 11 further comprising defining a predetermined area for measuring patient mobility.

20. The system of claim 19 further comprising defining the predetermined area for measuring patient mobility as the patient room.

* * * * *